United States Patent [19]

Haynes

[11] Patent Number: 4,725,442

[45] Date of Patent: Feb. 16, 1988

[54] MICRODROPLETS OF WATER-INSOLUBLE DRUGS AND INJECTABLE FORMULATIONS CONTAINING SAME

[76] Inventor: Duncan H. Haynes, 4051 Barbarossa Ave., Miami, Fla. 33133

[21] Appl. No.: 854,515

[22] Filed: Apr. 22, 1986

Related U.S. Application Data

[62] Division of Ser. No. 505,326, Jun. 17, 1983, Pat. No. 4,622,219.

[51] Int. Cl.$^4$ ............................ A61K 9/10; A61K 9/52
[52] U.S. Cl. ..................................... 424/490; 424/450;
514/965; 514/801; 514/816; 514/818; 514/906;
514/923; 514/869; 514/822
[58] Field of Search ............... 514/965, 801, 816, 818,
514/822, 869, 906, 923; 424/450, 490

[56] References Cited

U.S. PATENT DOCUMENTS

| | | | |
|---|---|---|---|
| 3,965,255 | 6/1976 | Bloch et al. | 424/450 |
| 4,016,100 | 4/1977 | Suzuki et al. | 424/450 |
| 4,078,052 | 3/1978 | Papahadjopoulos | 424/450 |
| 4,133,874 | 1/1979 | Miller et al. | 424/450 |
| 4,145,410 | 3/1979 | Sears | 424/450 |
| 4,186,183 | 1/1980 | Steck et al. | 424/450 |
| 4,241,046 | 12/1980 | Papahadjopoulos et al. | 424/450 |
| 4,529,561 | 7/1985 | Hunt et al. | 424/450 |
| 4,532,089 | 7/1985 | MacDonald | 424/450 |
| 4,622,219 | 11/1986 | Haynes | 514/818 |

Primary Examiner—Ronald W. Griffin
Attorney, Agent, or Firm—Nixon & Vanderhye

[57] ABSTRACT

Microdroplets of water-insoluble drugs coated with a phospholipid are prepared by sonication. As an example, microdroplets of the general anesthetic methoxyfluorane coated by a unimolecular layer of dimysistoyl phosphatidylcholine are prepared by sonication. The microdroplets so prepared remain stable in physiologically-compatible solution, and are suitable for injection, typically intradermally or intraveneously, into a patient for inducing local anesthesia. These methoxyflurane-containing microdroplets have been demonstrated to cause long-term local anesthesia when injected intradermally, giving duration of anesthesia 28 times longer than with other anesthetics, such as lidocaine and 11 times longer than with bupivacaine. The latter is considered longest acting conventional local anesthetic. The microdroplet is also capable of solubilizing and delivering benzocaine and other water-insoluble drugs, and thus represents a novel drug delivery system and general method for delivery of water-insoluble drugs, lowering the necessary dose and providing a more direct and timed release.

28 Claims, 5 Drawing Figures

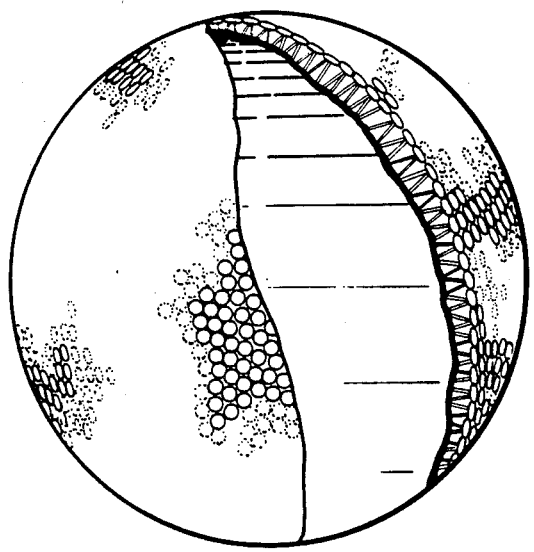
FIG. 1
FIG. 2
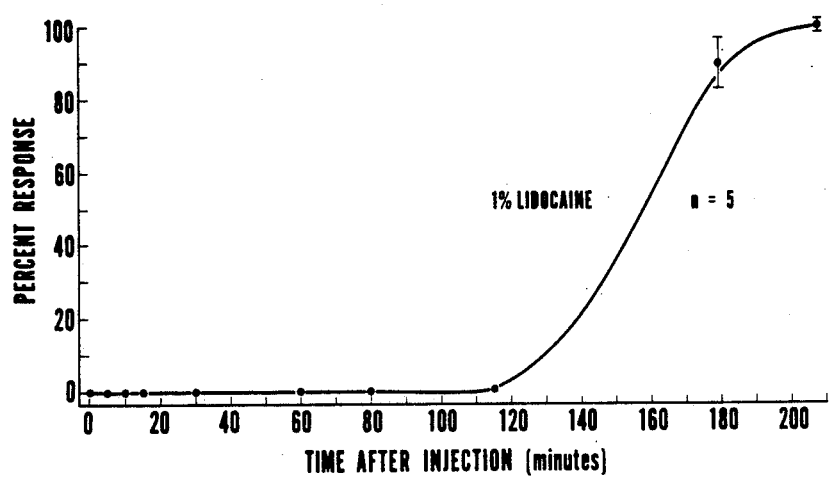

MICRODROPLETS OF WATER-INSOLUBLE DRUGS AND INJECTABLE FORMULATIONS CONTAINING SAME

This is a division of application Ser. No. 505,326 filed June 17, 1983, now U.S. Pat. No. 4,622,219, issued Nov. 11, 1986.

BACKGROUND OF THE INVENTION

Microdroplets, originally called monolayer vesicles, were previously used to study the properties of the phospholipid surface as a model for the true phospholipid vesicle which, in turn, was a model for the biological membrane. This approach is to be distinguished from liposomes (multilamellar-) and unilamellar phospholipid vesicles used to deliver water-soluble drugs to the interior of cells, both in vivo and in vitro. These liposomes are true vesicles and consist of a spherical lipid bilayer with an aqueous phase inside.

Microdroplets are known and consist of spheres of organic liquid phase drug approximately 500 Angstroms in diameter and range from 200 Angstroms up to at least one micron (10,000 Angstroms) in diameter and are covered with a monolayer of a suitable phospholipid.

The microdroplets of my invention can be used to deliver any water-insoluble/oil-soluble drug compound via injection. Most non-polar drugs now taken orally are contemplated and are within the scope of the invention. The organic liquid phase may be the drug itself, a general anesthetic medium, fluorocarbons, vegetable oil or mineral oil. The advantages of the microdroplets provided by my invention include a relatively slow release of the drug substance to the tissues and allow for a targeted delivery by intelligent choice of the site of injection with lowered metabolic degradation, first pass effects, and toxic side-effects in the liver and other organs.

Local anesthesia is conventionally accomplished by injection of water-soluble compounds into the site to be anesthetized. For efficacy the drugs need both hydrophobic properties, to bind to and cross cell membranes, and hydrophilic properties, to dissolve in water and diffuse to the site of action. The duration of anesthesia is limited by the fairly rapid process of absorption of the injected anesthetic into the blood. The currently-used example of a longacting local anesthetic is bupivacaine which gives anesthesia for a few hours in some applications. There is a considerable need for a local anesthetic of longer duration, preferably of significantly longer duration. Instances of the need for longer anesthetic duration include the control of post-operative pain, relief of chronic pain in cases of pinched nerves, back pain and other applications requiring long-term nerve conduction block and the like. Management of long-term pain is done by analgesics, such as aspirin and opiods, but these are often ineffective and sometimes give unwanted side-effects.

In contrast to local anesthesia is general anesthesia, which is accomplished by inhalation of anesthetic gases to produce unconsciousness. These include nitrous oxide, halothane, isoflurane, enflurane and methoxyflurane. The first-named example is a true gas; the others are volatile fluoro-chloro-hydrocarbons which exist in liquid form. Liquid general anesthetics are water-insoluble and immiscible. They are volatized into the air which the patient breathes, they gain access to the circulation through the lungs and cause unconsciousness by binding to the nerve membranes in the brain.

The novelty of one embodiment of my invention lies in the fact that it uses general anesthetics as local anesthetics. According to a current popular conception of physicians and biomedical scientists the use of inhalation anesthetics as local anesthetics is impossible. The textbooks and scientific papers deal with the local anesthetics and the general (often termed "volatile" and "inhalation" anesthetics) as separate classes of drug substances. According to contemporary thought this division is correct since the volatile anesthetics exist as oil-like liquids which are impossible to inject due to their low solubility in water—injection as such would be unthinkable. Injection of a liquid phase of any of the volatile anesthetics would result in membrane delipidation, cellular damage and eventual tissue necrosis. Dilution of such agents in saline is not feasible because of their water-insolubility. Yet it is this low water-solubility and high solubility in the membrane phase which makes these agents effective blockers of nerve conduction in the brain (and elsewhere, but with less physiological consequence).

BRIEF DESCRIPTION OF THE DRAWINGS

FIG. 1 is a perspective representation, partially broken away, of a microdroplet of the invention containing an organic liquid and drug substance surrounded by a unimolecular lecithin outer surface;

FIG. 2 is a graph based on the results of Example 1 comparing the percent response of 1% lidocaine over a period of up to 200 minutes following injection;

Figure 3:
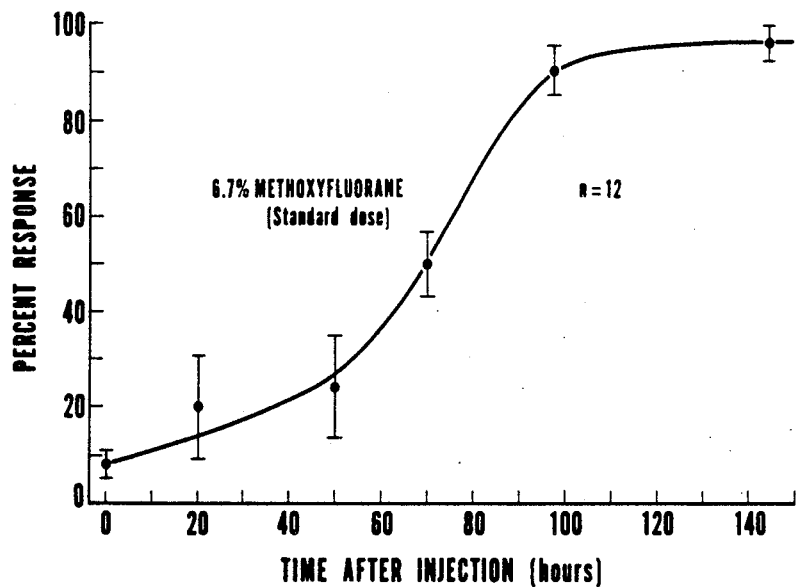
FIG. 3 is a graph reporting the response for Example 1 as the percent response of rats to a pain stimulus induced by the tail-clamp technique, as a function of time after injection of microdroplets of methoxyflurane.

The uniqueness of my invention is that a means of reducing the above-mentioned oil-like phase of a volatile anesthetic to microscopic droplets, for instance approximately 500 Angstroms (estimated by calculation) in diameter is now available. Moreover, these microscopic droplets are stabilized against coalescence by a monolayer of phospholipid. Upon intradermal injection these microdroplets become entrapped in the interstitial space between cells and release their anesthetic in a slow and sustained manner. While not wishing to be bound to any particular theory or mode of operation, three possible mechanisms are postulated for this: anesthetic diffusion, vesicle-cell membrane collision and fusion; see the discussion below. This is in contrast to normal elimination kinetics of an injected drug in which the drug is eliminated in a "first order" manner giving rise to an exponential decrease in concentration. With the controlled and sustained release, the concentration of the drug in the nerve and neighboring tissue does not reach toxic concentrations. The rate of release can be controlled by the choice of anesthetic agent, based on vapor pressure and membrane solubility, and to some extent by the choice of lipid.

One skilled in the art following the instructions provided herein will have no difficulty in empirically determining an optimum relationship between anesthetic agent or water-insoluble drug substance and compatible lipid coating. For the least exchangeable agents and most non-reactive lipids, the duration of effect will be governed by the time which it takes for the microdroplets to be cleared from the interstitial space and pass into the lymphatic system. The same principles are applicable to the use of lecithin-anesthetic microdroplets as a carrier for other water-insoluble drugs such as benzocaine, dantrolene and the like.

Local anesthesia requires delivery of the drug directly to the nerve membrane. This requires that the drug be able to bind to membranes and to traverse lipid membranes, i.e., cell membranes, and that it be water-soluble and thus able to cross the aqueous regions between cells in order to diffuse to the nerve membranes. These requirements have been fulfilled by designing local anesthetics, for example procaine and lidocaine, which have both non-polar and polar structural features. Their water-solubility results in limitation of the life-time (duration) of anesthetic effect since the local anesthetics diffuse to capillaries and are removed by the blood in the above-mentioned first order process. Theoretically, this problem could be circumvented by employing local anesthetics which are poorly soluble in water, e.g., benzocaine, but the problem then becomes the delivery of the anesthetic. Water-insoluble local anesthetics are not absorbed well through the skin and it is not possible to inject them as one injects the water-soluble ones.

As mentioned above, general anesthetics are gases and volatile liquids which are inhaled to produce unconsciousness. They are poorly water-soluble compounds which enter the bloodstream by absorption in the lungs and which are carried through the bloodstream by binding to blood cells and proteins. They work on the central nervous system because it is most susceptible to their action, given this mode of delivery.

A microdroplet in accordance with the present invention is represented in perspective, partially broken away, in FIG. 1, revealing a center containing the water-insoluble/organic phase containing the drug substance, surrounded by an outer unimolecular layer of lipid, such as lecithin. The properties of phospholipid membranes are described inter alia in my article concerning divalent cation-ligand interactions appearing in Metal-Ligand Interactions in Organic Chemistry and Biochemistry, Pullman and Goldblum, Part 2, pages 189–212, D. Reidel (1977).

One of the unique features of my invention lies in the use of volatile liquid general anesthetics to produce local anesthesia. Prior to this invention, it was not considered possible to inject an organic phase into the skin or other tissues without producing local damage due to dissolution of cell membranes and general derangement. Such a procedure would be literally unthinkable. My invention allows the injection of volatile general anesthetics without damage.

The key to accomplish the desired injection is accomplished by reducing the water-insoluble oil or anesthetic (liquid) phase to microscopic dimensions, typically by sonication, and then coating the resulting structure with a layer of a lipid. Preferred are the phospholipids, which are natural constituents of biological membranes and as such are biologically compatible. A phospholipid is chosen which exhibits repulsive interaction with the cell membranes in the target tissue such that the microdroplet remains integral for the maximum time.

Figure 4:
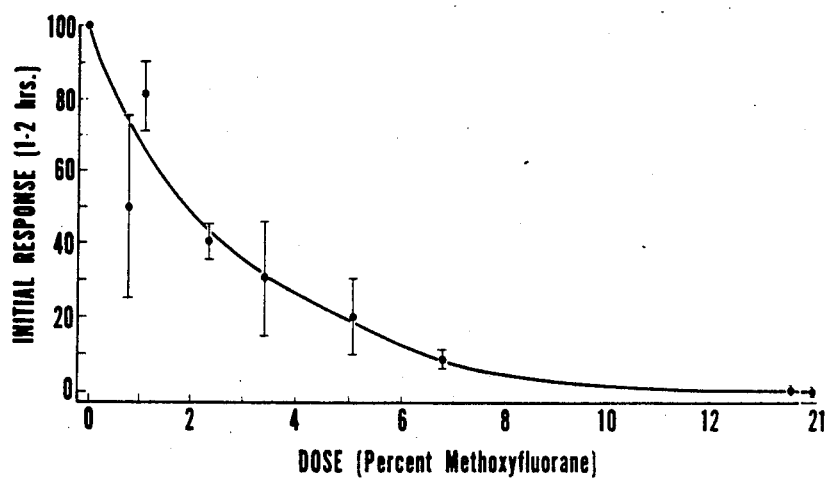
FIG. 4 is a graph also based on Example 1 reporting the initial response in percent against the dose of methoxyfluorane, in volume percent.
Figure 5:
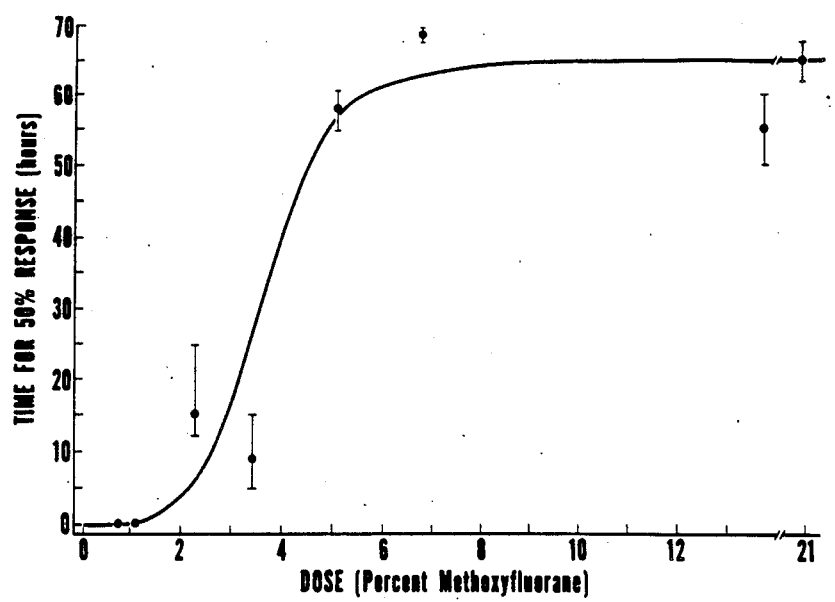
FIG. 5 is a graph also based on Example 1 reporting the time necessary for recovery of 50% response after the injection of microdroplets of methoxyfluorane against concentration of microdroplets, in volume percent.

As mentioned above, it is believed that the microdroplet can transfer anesthetic to the tissue and nerves by three possible mechanisms: (a) solution, (b) collision/aggregation, or (c) fusion. Comparisons of anesthethic response plotted against time in hours after injection are shown in FIG. 3. From this and from FIGS. 4 and 5 it can be deduced that the release of the anesthetic from the microdroplets is slow and sustained. FIG. 3 shows that the response of rats to pain stimulus induced by tail clamping is decreased by injection of 0.5 ml of 6.7% methoxyfluorane microdroplets. The initial responsiveness ($t=0–2\frac{1}{2}$ hrs) is also dose-dependent as shown in FIG. 4. The half-time for recovery of responsiveness increases with increasing anesthetic concentration, reaching a maximum of approximately 70 hours at high concentrations as shown in FIG. 5. The above are illustrative and demonstrate effectiveness using the anesthetics at variable doses at a number of sites on the rat. Lidocaine was used as a control. Durations of lidocaine anesthesia were always less than 1/10th that of preparations in accordance with my invention.

While the research work leading to the recognition and completion of the present invention has been conceived primarily with anesthetics, and will in large part be illustrated and explained herein on that basis, my invention is not so limited and includes similar systems employing water-insoluble organic drug substances included in the unique drug delivery systems and procedures of my invention.

Microdroplet preparation: The preferred method of preparing the microdroplets of the invention is by sonication with a probe sonicator. This is described in more detail below. Alternatively, microdroplets can be prepared in a bath sonicator. For small scale preparations a 1.0 cm diameter test tube is suspended, with use of a test-tube clamp, in a bath sonicator filled with water. The components of the microdroplet (organic phase, phospholipid, physiological saline, and drug to be included) are first grossly mixed by shaking, Vortex mixing, Polytron or other methods. The homogenized suspension is then introduced into the bath sonicator and sonicated for 1–2 hours. If the preparation is to be done on a large scale, it will be possible to omit the test tube and introduce the components of the microdroplet directly into the bath sonicator.

Microdroplets may also be produced by high intensity mechanical agitation. Useful methods include the Waring blender, the Polytron and high frequency shakers such as a commercial paint shaker.

An alternative method to consider is the solvent dilution method. The desired constituents of the microdroplets are dissolved at high concentration in ethanol or another oil- and water-miscible organic liquid. The ethanol solution is rapidly diluted into the physiological saline solution with vigorous mechanical agitation to insure rapid mixing. The ethanol dissolves in the aqueous phase while the other constituents cannot. The finely-dispersed constituents spontaneously form microdroplets; the ethanol can be conveniently removed by dialysis.

Microdroplets can also be formed by a process similar to spray painting. The constituents of the microdroplets are suspended and sucked into the intake of a commercial spray painter and the resulting spray bubbled through a saline solution to trap the microdroplets.

By judicious choice of methods and materials the diameter of the microdroplets is controlled between approximately 500 Angstroms to several micrometers by controlling the method, power and lipid to organic phase ratio. Increasing the power or the ratio tends to give smaller microdroplets. If natural or unsaturated lipids are used preparation is conducted in an atmosphere free from oxygen.

Selection of organic phases: Microdroplets according to the present invention are prepared from a wide variety of organic phases which, for convenience, may be considered by the following non-limiting types or categories:

1. Volatile inhalation anesthetics include methoxyfluorane as well as halothane, isofluorane and enfluorane.

2. Alkanes include heptane. The heptane microdroplets can incorporate benzocaine which is suitable to produce long-duration local anesthesia. Higher molecular weight alkanes will also be potent. Mineral oil as the organic phase is also of interest as it is able to carry large quantities of water-insoluble drugs. Solubility may be increased by inclusion of more polar organic compounds with the alkane phase.

3. Natural, plant-derived "oils" are also broadly contemplated, including olive oil and various vegetable oils. The "oils" are preferably screened toxicologically.

4. Ethers: Microdroplets have been made from dipropyl ether (3.4 mg/ml dimyristoyl lecithin, 6.5% n-dipropyl ether, ±4.1 mg/ml benzocaine) and dibutyl ether (5 mg/ml dimyristoyl lecithin, 7.0% n-dibutyl ether, ±4.1 mg/ml benzocaine). The dibutyl ether microdroplets and mixed dibutyl ether/chloroform microdroplets were found to have anesthetic potency. However, the anesthesia was of shorter duration (approximately ½ hour) possibly due to the greater water solubility of the dibutyl ether and chloroform which contributed to its more rapid removal. Longer-chain analogues could yield longer durations of activity.

5. Esters: Any long-chain or hydrophobic ester is contemplated particularly as a useful device for delivering "pro-drugs" which would be transformed into the active drug by hydrolysis by serum or cellular esterases.

6. Other organic substances which have been shown to be bio-compatible. These include by way of example silicone and high molecular weight fluorocarbons.

The organic phase selected will be fully compatible with the drug substance employed and pharmaceutically acceptable for product formulation/preparation purposes. As with all medical applications once the microdroplets are successfully prepared from a given organic phase and the selected drug substance incorporated therein, toxicological and efficacy screening is routine. Preferably the various components from which the microdroplets are made are subjected to toxicological screening as well.

Lipids: Various lipids are also suitable for use in preparing the microdroplets of the present invention. Mixtures of two or more such lipids are useful to vary the surface properties and reactivity. All of the microdroplets in the working examples reported herein are made primarily from lecithin (phosphatidylcholine). This, together with sphingomyelin which is also contemplated, constitutes Class A. In Class B, are listed the phospholipids which can also be used to make microdroplets in the pure form, but which will react with calcium in the serum to give microdroplet aggregation or binding to cell membranes. The tendency to do this can be decreased by dilution with phosphatidylcholine, and thus there is a means of controlling the reactivity of the microdroplet. Class C contains only one representative, phosphatidylethanolamine. In the pure state it self-aggregates in a calcium-independent fashion. It is expected to have strong tendencies to aggregate with cell membranes. This tendency can be decreased by diluting it with lecithin. Class D, the steroids, do not form membranes or microdroplets by themselves, but which can be incorporated into the membrane, increasing its stability and decreasing its reactivity. Class E includes all molecules which can be accommodated in the monolayer. These are amphipathic molecules which can serve to change the nature of the monolayer surface and microdroplet reactivity.

CLASS A: Primary Lipids (usable in pure form) include the following:
Lecithin (phosphatidylcholine)
Sphingomyelin CLASS B: These can be used in the pure form to make microdroplets (or phospholipid vesicles). They are expected to be highly reactive because of calcium-dependent aggregation. Preferably these lipids are mixed with lecithin to obtain controlled degrees of reactivity with cell membranes. Mixing in phospholipid vesicle preparations has already been demonstrated. These phospholipids include the following:
Phosphatidic acid
Phosphatidyl serine
Phosphatidyl inositol
Cardiolipin (diphosphatidyl glycerol)
Phosphatidyl glycerol CLASS C: Phosphatidyl ethanolamine. This can be used to make microdroplets in the pure form at pH 9; they will self-aggregate when brought to pH 7. This has been shown to be feasible in phospholipid vesicle studies. Microdroplets made from phosphatidyl ethanolamine are expected to be very reactive with cell membranes. It is suggested that this lipid can be included with the normal lecithin to increase the reactivity to cell membranes.

CLASS D: Steroids. These should not be used in the pure form to make microdroplets but can be mixed with lecithin or other lipids to produce a surface which is less reactive, and presumably more stable. These steroids include the following:
Cholesterol (natural constituent of membranes)
Estrogens: Estriol, estrone, estradiol and diethylstilbestrol
Androgens: Androstenedione, testosterone (The microdroplet would also constitute a delivery system for estrogens and androgens.)

CLASS E: Semi-lipoidal molecules which can incorporate into the monolayer and change the surface activity of the microdroplet. These molecules could also be delivered to the nerve by the microdroplet. Molecules included in this class are the following:
Stearylamine or other long-chained alkyl amines which can be primary, secondary, tertiary or quaternary substituted. These give the microdroplet surface a positive charge and make them more reactive for the cell membranes. These compounds could also be delivered to the nerve.
Arachidonic acid or fatty acids. These could be incorporated into the microdroplet surface giving altered lipid packing and increased reactivity with cell membranes. The microdroplet is also a means of delivery of arachidonic acid for manipulations of prostaglandins.

CLASS F: Membrane-active agents including Nystatin, amphotericin B and gramicidin. These are surface-active antibiotics which have been shown to bind to the surfaces of phospholipid membranes and change their permeability. They are expected to change the reactivity of the microdroplet. The microdroplet is also a means of subcutaneous delivery of these antibiotics.

Several forms of lecithin are contemplated. For example lecithin is available as egg or bovine heart lecithin (natural) or in several synthetic varieties which differ in chain length. These include chain lengths ranging from 4 to 19 carbons (Supelco, Inc.). Dimyristoyl (14 carbons) and didodecanoyl (12 carbons) lecithin were used in the working examples (below). Didodecanoyl lecithin (12 carbons) may be considered more useful because the microdroplets will be more resistant to aggregation below room temperature. It is believed that lecithins with chain lengths in the biological range (10–18 carbons) are useful in various applications. Unsaturated lecithins (dioeoyl), dilinoeoyl; alpha-palmito, beta oleoyl; alpha palmitoyl beta linoleoyl and alpha oleoyl beta palmitoyl) are also available. Diarachidonyl lecithin (highly unsaturated and a prostaglandin precursor) is also available, as is alpha palmito beta myristoyl (mixed unsaturated chains) lecithin.

Phosphatidic acid is available from egg or as synthetic compounds (dimyristoyl, dipalmitoyl or distearoyl, Calbiochem). Bovine phosphatidyl serine is available (Supelco or Calbiochem).

Phosphatidyl inositol is available from plant (Supelco) or bovine (Calbiochem) sources. Cardiolipin is available (Supelco) from bovine or bacterial sources. Phosphatidyl glycerol is available from bacterial (Supelco) sources or as synthetic compounds (dimyristoyl or dipalmitoyl; Calbiochem).

Phosphatidyl ethanolamine is available as egg, bacterial, bovine, or plasmalogen (Supelco) or as synthetic compounds dioctadecanoyl and dioleoyl analogues and dihexadecyl, dilauryl, dimyristoyl and dipalmitoyl (Supelco and Calbiochem).

Drugs: The following is a list of drug substances which may be incorporated into the micro-droplets of the invention. This list is presented for purposes of illustration only and is not to be considered as limiting.

1. The volatile anesthetics are described above. They include methoxyflurane, isoflurane, enfluorane and halothane. Heptane was also shown to have anesthetic potency.

The following drugs will be incorporated primarily in the organic phase of the microdroplet. They are all uncharged, lipophilic water-insoluble drugs which have high oil solubility. In their applications, the organic phases of the microdroplets are made from the organic phase demonstrating the greatest drug solubility in macroscopic tests.

2. Water-insoluble local anesthetics. At a level of 2 mg/ml benzocaine can be incorporated into a 10% heptane microdroplet suspension (8.3 mg/ml dimyristoyl lecithin).

3. Dantrolene, a direct-acting muscle relaxant, is incorporated into methoxyfluorane microdroplets, heptane or mineral oil microdroplets. The resulting microdroplet suspension is injected around muscles and nerves for control of spasticity. This could circumvent the problem of hepatic toxicity seen with chronic oral administration of the drug.

4. The barbiturates (barbituric acid, pentothanl, phenobarbital, etc.) have been shown to block ganglionic transmission. The hypnotic/sedatives of the benzodiazepine class (diazepam, oxazipam, etc.) are presently used as muscle relaxants. These effects could be amplified by direct injection via microdroplets and the central nervous system effects obviated.

5. The microdroplet is believed to be an excellent means of direct and targeted administration of anti-inflammatory agents. Phenylbutazone can be administered at high concentration at the site of inflammation. The side-effects of nausea and vomiting, typically seen with oral administration, would be largely circumvented and much higher local doses could be used. Other anti-inflammatory or anti-arthritic agents which could be used include acetaminophen and colchincine.

6. Present evidence suggests that the rate of release of water-insoluble substances from the microdroplets to the blood stream will be slow if the microdroplets are injected intradermally or intramuscularly. This slow release is believed to be useful for the following classes of drugs:

(a) cardiovascularly active drugs: propranolol, labetalol, reserpine, nitroglycerin;
(b) hormones: estrogens, androgens, anabolic steroids in cancer chemotherapy;
(c) spironolactone (diuretic);
(d) coumarin (and other oral anti-coagulants);
(e) oil-soluble vitamins;
(f) prostaglandins and their analogues.

7. There are a number of drugs which are suitable for incorporation into microdroplets but the advantages of this treatment form with intradermal or intramuscular injection are not particularly apparent at present. These include the following: tricyclic anti-depressants, phenytoin (antiepileptic), and other centrally-acting agents.

All parts and percentages reported herein are by weight and all temperatures reported in degrees Celsius, unless otherwise indicated. The compositions of the invention can comprise, consist essentially of or consist of the materials set forth and the process or method can comprise, consist essentially of or consist of the steps set forth with such materials.

DETAILED DESCRIPTION OF THE INVENTION

EXAMPLE 1

Anesthetic-containing lecithin-coated microdroplets are prepared by sonication in the following manner. Dimyristoyl phosphatidylcholine (41 mg) is added to a test tube and methoxyflurane (0.2 ml) is pipetted in. The mixture is swirled in the tube at approximately 37° C. and the lipid is observed to dissolve or be suspended to a limited extent. Next, sterile physiological saline (3.0 ml) is added and the tube is suspended under a Sonifier® Cell Disrupter, Model W185D (Heat System and Ultrasonics, Plainview, N.Y.). The microtip is inserted and the sample is sonicated gently (power stage 2) for approximately one minute until the sample is dispersed. The oil, solid and aqueous phases are not distinguishable and gross homogeneity is obtained. The result appears as a milky single phase.

Next, the power is increased to stage 4 and the sample is sonicated for a total of approximately 5 minutes. The sonication temperature is between 30° and 45° C. The temperature can be controlled either by circulation of coolant around the sonication vessel or by interrupting the sonication periodically and allowing the sample to cool. The result of the sonication is a stable, homogenous suspension of lecithin-methoxyfluorane microdroplets. At the stated concentration, the suspension appears slightly cloudy to the eye; turbidity decreases with increasing dilution of the sample in accordance with Beer's Law. Efficacy and microdroplet properties do not depend on the concentration at which the microdroplets were prepared, as observed from experiments carried out over a wide range of concentrations. The preparation is stable for several days when stored at 30° C. The preparation retains the smell of methoxy-flurane indicating that component is there and is releasable. Control experiments in which the lecithin is omitted from the medium failed to give microdroplets; phase separation was obtained immediately.

The efficacy of the preparation was tested with laboratory rats using a tail-clamp assay according to the method of Munson et al; [Munson, E. S, Hoffman, J. C. and DiFazio, C. A. "The Effects of Acute Hypothyroidism and Hyperthyroidism on Cyclopropane Requirement (MAC) in Rats" Anesthesiology 29: 1094–1098 (1968).] The anesthetic preparation was injected into the tail and injections were distributed over four sites (0.5 ml total) such that a 3–4 cm long weal was obtained, eccompassing all sides of the tail. Anesthesia was determined as being either present or absent from the response of the animal to clamping of the treated area with forceps as visually observed by squeeks or rapid movement. Untreated areas of the tail served as the control for the responsiveness of the animal to pain. As additional controls, some of the animals were injected with saline or sonicated lecithin without anesthetic agents. These controls showed uniformly no effect.

The efficacy of the microdroplet preparation was compared with that of 0.5 ml of 1% lidocaine (FIG. 2) and bupivacaine in separate animals treated and tested in parallel. At least four animals were assigned to each treatment and dosage group. They were tested immediately after treatment and at timed intervals thereafter until complete responsiveness was obtained in all animals.

With lidocaine, the animals were rendered 0% responsive. On the time scale presented, the effect wore off rapidly. After 2.5 hours the animals were 50% responsive and no measurable effect is observed after six hours. A similar experiment was carried out using 0.5% bupivacaine which is the longest acting local anesthetic in clinical use. A similar response was observed (data not shown), the animals became 50% responsive after 6.5 hours and there was no measurable effect after 8 hours.

The results are shown in FIG. 3 which illustrates the responsiveness of the 12 animals to the pain stimulus for the lecithin-methoxyfluorane microdroplet (1.28% lecithin, 6.25% methoxyfluorane) and for 1% lidocaine. "Responsiveness" is averaged for all animals (100=full pain response in all animals; 0%=no pain response in all animals). This Figure shows the responsiveness as a function of time after treatment. In the period of 1 to 2.5 hours after injection the animals were rendered 8% responsive to the pain stimulus. The effect persists during the times that the lidocaine effect had worn off (cf. FIG. 2).

Half-responsiveness was observed 70 hours after injection. The effect slowly wears off, with 100% responsiveness observed after approximately 140 hours, i.e., about six days.

FIG. 4 shows the dependence of the initial responsiveness as a function of the dose. FIG. 5 shows the half-time for return to 50% responsiveness and shows a sigmoidal dependence on the dose of methoxyflurane microdroplets, reaching a maximal half-time of 70 hours. Both the initial responsiveness effects and the half-time effects depend on the microdrop concentration in a graded manner consistent with the proposed mechanism of action: Large doses create large reservoirs of anesthetic within the tissue which must be removed before responsiveness to pain stimuli can be observed. Smaller doses can be used to create marginal anesthesia for a shorter time. In the latter case the injected dose of microdroplets does not have sufficient reservoir capacity to saturate the tissue. The maximal half-time for return of responsiveness of approximately 70 hours observed at maximal dose is believed to reflect the time that it takes the vesicles to be cleared from the tissue via the lymphatics.

EXAMPLE 2

Example 1 was repeated this time using 6.7% n-heptane as the anesthetic and similar results were obtained.

EXAMPLE 3

Example 1 was repeated this time using microdroplets with a 1:1 mixture of n-dibutyl ether and chloroform as the organic phase (6.7%) but the anesthesia was of short duration (1–2 hours). This correlates with the increased volatility and water solubility of these agents which give more rapid removal via the blood. The n-dibutyl ether chloroform microdroplets were shown to be effective in solubilizing benzocaine, but no increased efficacy of anesthesia was observed.

EXAMPLE 4

Lecithin coated methoxyflurane microdroplets were injected into the hind leg muscles of the rat (2.0 ml total dose) and this resulted in immobilization of its hind quarters for one day. Controlled injections of lidocaine gave only short-duration immobilization (approximately two hours).

EXAMPLE 5

Microdroplets were prepared as described in Example 1 except that the organic phase consisted of 6.7% mineral oil and the phospholipid monolayer consisted of didocecanoyl (dilauryl) lecithin (12.8 mg/ml). The microdroplets were found to be stable at 37° C. in vitro for over a month. The microdroplets were injected into the tails of two rats and no toxic effects were observed. Local anesthesia was not observed, in accordance with expectations since mineral oil lacks anesthetic potency.

EXAMPLE 6

Microdroplets were prepared as described in Example 1 except that the organic phase consisted of 2.42% methoxyflurane, 2.42% n-dibutyl ether and 1.8% mineral oil solubilizing 1.8 mg/ml benzocaine and the phospholipid monolayer consisted of didocecanoyl (dilauryl) lecithin (12.8 mg/ml). The microdroplets were found to be stable at 37° C. in vitro for over a month. The microdroplets were injected into the tails of two rats and no toxic effects were observed. Local anesthesia was observed with kinetics similar to that given in FIGS. 4 and 5 for 2.4% methoxyflurane.

I claim:

1. A microdroplet of from about 200 Angstroms up to one micron in diameter consisting essentially of a sphere of a substantially water-insoluble, pharmacologically acceptable liquid drug substance surrounded by a layer of phospholipid.

2. A microdroplet of from about 200 angstroms up to one micron in diameter consisting essentially of a sphere of a substantially water-insoluble drug substance dissolved in a compatible, pharmaceutically acceptable organic liquid selected from an alkane, a dialkyl ether, a long-chain ester, a hydrophobic ester, a biocompatible silicone, a biocompatible high molecular weight fluorocarbon, an oil-soluble vitamin and a volatile liquid anesthetic, the liquid plus drug being surrounded by a layer of phospholipid.

3. A microdroplet of from about 200 Angstroms up to one micron in diameter consisting essentially of a sphere of a liquid drug substance together with a compatible, pharmaceutically acceptable organic liquid selected from a volatile liquid anesthetic, an alkane, a dialkyl ether, a long-chain ester, a hydrophobic ester, a biocompatible silicone and a biocompatible high molecular weight fluorocarbon, the liquid plus liquid drug being surrounded by a layer of phospholipid.

4. An injectable pharmaceutical composition consisting essentially of the microdroplets of claim 1, 2 or 3 together with a pharmaceutically acceptable injectable vehicle.

5. The injectable pharmaceutical composition of claim 4, in which the injectable vehicle is an isotonic solution.

6. The microdroplet of claim 1, 2 or 3 in which the drug substance is a general anesthetic in liquid form.

7. The microdroplet of claim 1, 2 or 3 in which the drug substance is a water-insoluble local anesthetic.

8. The microdroplet of claim 1, 2 or 3 in which the drug substance is a muscle relaxant.

9. The microdroplet of claim 1, 2 or 3 in which the drug substance is a hypnotic/sedative or analgesic.

10. The microdroplet of claim 1, 2 or 3 in which the drug substance is a non-steroidal anti-inflammatory agent.

11. The microdroplet of claim 1, 2 or 3 in which the drug substance is a steroidal anti-inflammatory agent.

12. The microdroplet of claim 1, 2 or 3 in which the drug substance is a membrane-binding, lipophilic antibiotic.

13. The microdroplet of claim 1, 2 or 3 in which the drug substance is a cardiovascularly active drug.

14. The microdroplet of claim 1, 2 or 3 in which the drug substance is a hormone.

15. The microdroplet of claim 1, 2 or 3 in which the drug substance is a cancer therapeutic agent.

16. The microdroplet of claim 1, 2 or 3 in which the drug substance is a diuretic.

17. The microdroplet of claim 1, 2 or 3 in which the drug substance is an anticoagulant.

18. The microdroplet of claim 1, 2 or 3 in which the drug substance is an oil-soluble vitamin.

19. The microdroplet of claim 1, 2 or 3 in which the drug substance is a prostaglandin.

20. The microdroplet of claim 1, 2 or 3 in which the drub substance is a tricyclic antidepressant.

21. The microdroplet of claim 1, 2 or 3 in which the drug substance is an antiepileptic.

22. A microdroplet, produced by sonification, of from about 200 Angstroms to one micron in diameter and consisting of a water-insoluble liquid drug core stabilized against coalescence and surrounded by a phospholipid layer in which the ratio of volume of drug substance to the weight of the phospholipid layer is at least 1.0 ml/g.

23. The microdroplet of claim 22, having a diameter of up to 10,000 Angstroms.

24. A timed release drug delivery vehicle composed of microdroplets of from about 200 Angstroms up to one micron in diameter consisting essentially of a substantially water-insoluble drug substance, itself a liquid or dissolved in a water-insoluble liquid, stabilized against coalescence and surrounded by a layer of phospholipid.

25. A sterile, injectable pharmaceutical composition consisting essentially of:

(1) microdroplets of from about 200 Angstroms to one micron in diameter produced by sonification and consisting of a water-insoluble local anesthetic or a solution thereof as the core stabilized against coalescence and surrounded by a phospholipid membrane layer, the ratio of the volume of liquid local anesthetic to the weight of the phospholipid membrane layer is at least 1.0 ml/g, and (2) a pharmaceutically acceptable injectable carrier.

26. A sterile, injectable pharmaceutical composition consisting essentially of:

(1) microdroplets of from about 200 Angstroms to one micron in diameter produced by sonification and consisting of a water-insoluble general anesthetic in liquid form as the core stabilized against coalescence and surrounded by a phospholipid membrane layer, the ratio of the volume of general anesthetic to the weight of the phospholipid is at least 1.0 ml/g, and (2) a pharmaceutically acceptable injectable carrier.

27. The pharmaceutical composition of claim 26, in which a substantially water-insoluble, non-anesthetic drug substance is solubilized in the liquid general anesthetic.

28. A timed release drug delivery vehicle composed of microdroplets of from about 200 Angstroms to 10,000 Angstroms in diameter consisting essentially of a water-insoluble drug substance, itself a liquid or dissolved in a water-insoluble liquid, stabilized against coalescence and surrounded by a layer of phospholipid in which the ratio of the volume of drug substance to the weight of the phospholipid is at least 1.0 ml/g.

* * * * *